United States Patent
Hamada et al.

(10) Patent No.: US 9,309,544 B2
(45) Date of Patent: Apr. 12, 2016

(54) METHOD FOR PRODUCING FATTY ACID ESTER

(71) Applicant: KAO CORPORATION, Tokyo (JP)

(72) Inventors: Saki Hamada, Wakayama (JP); Hiroyuki Konishi, Wakayama (JP); Takaaki Watanabe, Wakayama (JP)

(73) Assignee: KAO CORPORATION, Tokyo (JP)

( * ) Notice: Subject to any disclaimer, the term of this patent is extended or adjusted under 35 U.S.C. 154(b) by 46 days.

(21) Appl. No.: 14/382,688

(22) PCT Filed: Apr. 1, 2013

(86) PCT No.: PCT/JP2013/059886
§ 371 (c)(1),
(2) Date: Sep. 3, 2014

(87) PCT Pub. No.: WO2013/153981
PCT Pub. Date: Oct. 17, 2013

(65) Prior Publication Data
US 2015/0056671 A1 Feb. 26, 2015

(30) Foreign Application Priority Data

Apr. 10, 2012 (JP) .................. 2012-089648

(51) Int. Cl.
*C12P 7/62* (2006.01)
*C12P 7/64* (2006.01)
*C07B 41/02* (2006.01)

(52) U.S. Cl.
CPC .............. *C12P 7/6436* (2013.01); *C07B 41/02* (2013.01); *C12Y 304/21* (2013.01); *Y02P 20/52* (2015.11)

(58) Field of Classification Search
None
See application file for complete search history.

(56) References Cited

U.S. PATENT DOCUMENTS

| 6,180,376 B1 | 1/2001 | Liddell |
| 2004/0067574 A1 | 4/2004 | Bijl et al. |
| 2008/0194810 A1 | 8/2008 | Kim et al. |
| 2013/0115666 A1 | 5/2013 | Arashida et al. |
| 2013/0217924 A1 | 8/2013 | Konishi et al. |

FOREIGN PATENT DOCUMENTS

| JP | 59-118090 A | 7/1984 |
| JP | 60-197626 A | 10/1985 |
| JP | 62-190090 A | 8/1987 |
| JP | 3-227939 A | 10/1991 |
| JP | 5-027384 B2 | 4/1993 |
| JP | 10-004953 A | 1/1998 |
| JP | 2002-256281 A | 9/2002 |
| JP | 2010-090065 A | 4/2010 |
| JP | 2011-050279 A | 3/2011 |
| WO | WO 2012/011421 A1 | 1/2012 |
| WO | WO 2012/077717 A1 | 6/2012 |

OTHER PUBLICATIONS

Tucci "Variability of Wax Ester Fermentation in Natural and Bleached Euglena gracilis Strains in Response to Oxygen and the Elongase Inhibitor Flufenacet" Journal of Eukaryotic Microbiology (2010), 57(1) 63-69.*
International Search Report issued in PCT/JP2013/059886, mailed on Jun. 18, 2013.
International Preliminary Report on Patentability and English translation of the Written Opinion of the International Searching Authority (Forms PCT/IB/338, PCT/IB/373 and PCT/ISA/237), dated Oct. 23, 2014, for International Application No. PCT/JP2013/059886.

* cited by examiner

*Primary Examiner* — Louise W Humphrey
*Assistant Examiner* — Charles Zoltan Constantine
(74) *Attorney, Agent, or Firm* — Birch, Stewart, Kolasch & Birch, LLP

(57) ABSTRACT

Provided is a method of producing a fatty acid ester in a high yield through a simple operation using *Euglena* as a material. The method of producing a fatty acid ester comprises the following steps (a) and (b): (a) adding 0.001 to 9.5 [PU/g-dry cell] of at least one kind of protease to *Euglena* to react the *Euglena* and the protease in an aqueous phase; and (b) performing phase separation and collection of a fatty acid ester from a reaction liquid of the step (a).

20 Claims, No Drawings

METHOD FOR PRODUCING FATTY ACID ESTER

FIELD OF THE INVENTION

The present invention relates to a method of producing a fatty acid ester.

BACKGROUND OF THE INVENTION

In recent years, with a growing consciousness of and a growing interest in environmental issues such as global warming, reduction of carbon dioxide emissions and reduction of a concentration of carbon dioxide in air by fixation of carbon dioxide have been great challenges. Therefore, attempts to break dependence on fossil fuels and to actively utilize a biomass, which is a carbon neutral source, as an energy source have been made actively.

For example, *Euglena* is known as an alga producing a lipid or the like in the cells. With focusing attention on lipid productivity thereof, there has been proposed a method involving: culturing *Euglena* aerobically; then placing the resultant under an anaerobic condition to convert a storage polysaccharide paramylon into a wax ester; physically breaking the resultant; and then isolating the wax ester by centrifugation, solvent extraction or the like (Patent Document 1). Further, there is known a method involving: heating and pressurizing *Euglena* using an autoclave; allowing a high concentration of a protease to act on the *Euglena*; and fractionating a water-soluble component by filtration. However, fractionation of a water-insoluble component has not been examined (Patent Document 2).

CITATION LIST

Patent Document

[Patent Document 1] JP-A-59-118090
[Patent Document 2] JP-A-2010-90065

SUMMARY OF THE INVENTION

The present invention provides a method of producing a fatty acid ester, comprising the following steps (a) and (b):
(a) adding 0.001 to 9.5 [PU/g-dry cell] of at least one kind of protease to *Euglena* to react the *Euglena* and the protease in an aqueous phase; and
(b) performing phase separation and collection of a fatty acid ester from a reaction liquid of the step (a).

DETAILED DESCRIPTION OF THE INVENTION

The inventors of the present invention tried to subject *Euglena* to physical crushing or treatment with a high concentration of protease to fractionate a water-insoluble fatty acid ester taken out of the cells of the *Euglena*, and found that it was difficult to improve the yield of the fatty acid ester, and, in particular, that the yield of the fatty acid ester was significantly lowered in the case of allowing a high concentration of protease to act on the *Euglena*.

Therefore, the present invention relates to providing a method of producing a fatty acid ester in a high yield through a simple operation using *Euglena* as a material.

The inventors of the present invention made studies to achieve the above-mentioned object, and as a result, surprisingly found that when a protease was allowed to act on *Euglena* in a much smaller amount than ever before, a fatty acid ester was able to be collected from the *Euglena* in a high yield.

According to the present invention, a fatty acid ester can be produced in a high yield through a simple operation using *Euglena* as a material.

The method of producing a fatty acid ester of the present invention includes the following steps (a) and (b). The steps are described below in detail.

Step (a)

The step (a) is a step of adding 0.001 to 9.5 [PU/g-dry cell] of at least one kind of protease to *Euglena* to react the *Euglena* and the protease in an aqueous phase. This can take the fatty acid ester in the cells out of the cells.

<*Euglena*>

The *Euglena* used in the present invention is a kind of microalgae belonging to the genus *Euglena* and is classified into both of animals and plants. The *Euglena* is a microorganism belonging to the class Mastigophorea in zoology and to the class Euglenophyceae in botany. Specific examples thereof include *Euglena gracilis, Euglena gracilis* var. *bacillaris, Euglena viridis, Astasia longa* and the like, and the *Euglena* includes variant species and mutant strains of strains having substantially the same algological properties as the strains described above. Of those, *Euglena gracilis, Euglena gracilis* var. *bacillaris, Euglena viridis, Astasia longa*, or a variant species or mutant strain thereof is preferred from the viewpoint of easy handling.

The *Euglena* used in the present invention may be *Euglena* that lives in and is collected from natural environments such as swamp and pond, one cultured in a conventionally known medium, or a commercially available one. In the present invention, *Euglena* including a large amount of a fatty acid ester accumulated in the cells is suitably used.

The *Euglena* used in the present invention is *Euglena* having a content of a fatty acid ester, which is accumulated in the cells, of preferably 20 mass % or more, more preferably 40 mass % or more, even more preferably 50 mass % or more based on the dry cells of the *Euglena*, from the viewpoint of the amount of the fatty acid ester produced per cell. On the other hand, the *Euglena* used in the present invention is *Euglena* having a content of a fatty acid ester, which is accumulated in the cells, of preferably 90 mass % or less, more preferably 85 mass % or less, even more preferably 80 mass % or less based on the dry cells of the *Euglena*, from the viewpoint of shortening the time for culture of the *Euglena* or availability of the *Euglena*.

The content of the fatty acid ester accumulated in the cells of the *Euglena* ranges preferably from 20 to 90 mass %, more preferably from 40 to 85 mass %, even more preferably from 50 to 80 mass % based on the dry cells of the *Euglena*, from the viewpoints of the amount of the fatty acid ester produced per cell and shortening the time for culture of the *Euglena* or availability of the *Euglena*.

The fatty acid ester accumulated in the cells of the *Euglena* is, for example, an ester of a fatty acid having 10 to 30 carbon atoms and a higher alcohol having 10 to 20 carbon atoms. The term "fatty acid ester" as used herein refers to a collective term for esters of fatty acids and monohydric, dihydric and trihydric alcohols and refers to a concept including a glyceride, which is an ester of a higher fatty acid and glycerin, and a wax, which is an ester of a fatty acid and a higher alcohol. It should be noted that the fatty acid may be a saturated fatty acid or an unsaturated fatty acid, and is preferably a saturated linear fatty acid. Of those, a fatty acid ester of a fatty acid having 10 to 20 carbon atoms and a higher alcohol having 10 to 16 carbon atoms is preferred. Specific examples of the fatty acid include decanoic acid, dodecanoic acid, tetradecanoic acid, pentadecanoic acid, hexadecanoic acid, heptadecanoic acid, octadecanoic acid, arachidic acid, arachidonic acid, behenic acid, erucic acid, triacontanoic acid and the like. In addition, specific examples of the higher alcohol include decanol, dodecanol, tridecanol, tetradecanol, cetyl alcohol, icosanol and the like. In addition, specific examples of the fatty acid ester may include dodecyl decanoate, dodecyl dodecanoate, tetradecyl dodecanoate, dodecyl tetradecanoate, tetradecyl tetradecanoate, hexadecyl tetradecanoate, octadecyl tetradecanoate, dodecyl hexadecanoate, tetradecyl hexadecanoate, hexadecyl hexadecanoate, octadecyl hexadecanoate and the like.

*Euglena* including a preferred amount of fatty acid ester in the cells can be obtained also by subjecting supplied *Euglena* to a step of accumulating a fatty acid ester in the cells of the *Euglena* by culture. Specifically, the following method is given.

Examples of the medium may include Cramer-Myers medium, Hutner medium, Koren-Hutner medium ("*Euglena*, physiology and biochemistry" edited by Shozaburo Kitaoka, Japan Scientific Societies Press, p. 242-243) and the like.

Further, there may be used a solid medium, liquid medium or the like supplemented with: a carbon source such as glucose, arabinose, xylose, mannose, fructose, galactose, sucrose, maltose, lactose, sorbitol, mannitol, inositol, glycerin, soluble starch, blackstrap molasses, inverted sugar syrup, an assimilable organic acid such as acetic acid or ethanol; and a nitrogen source such as an inorganic or organic ammonium salt including ammonia, an ammonium salt and the like, corn gluten meal, soybean powder, a yeast extract, a meat extract, a fish extract, polypeptone, any of various amino acids or soybean meal, and as required, further supplemented with: an inorganic salt of phosphoric acid, $Mg^{2+}$, $Ca^{2+}$, $Mn^{2+}$, $Zn^{2+}$, $Fe^{2+}$, $Fe^{3+}$, $Na^+$, $K^+$ or the like; and a vitamin such as vitamin B1 or vitamin B12.

The amount of the *Euglena* inoculated in the medium is not particularly limited, and is preferably from 0.01 to 10 [g-dry cell/L], more preferably from 0.1 to 5 [g-dry cell/L], with respect to the volume of the medium.

The culture method is not particularly limited, and for example, aeration culture, anaerobic culture, agitation culture, shaking culture, static culture and the like may be adopted. Of those, from the viewpoint of the improvement of the productivity of the fatty acid ester, it is preferred that the *Euglena* be cultured under an aerobic condition and then cultured under an anaerobic condition.

When the *Euglena* is cultured under an aerobic condition, the culture temperature is preferably from 20 to 33° C., more preferably from 28 to 30° C. The initial pH (at 25° C.) of the medium is preferably from 2 to 7, more preferably from 3 to 5.

Further, the aeration condition is preferably from 0.01 to 2 L/min, more preferably from 0.1 to 0.5 L/min per liter of a culture solution.

The culture period under the aerobic condition is preferably from 48 to 720 hours, more preferably from 72 to 360 hours.

On the other hand, when the *Euglena* is cultured under an anaerobic condition, the culture temperature is preferably from 20 to 33° C., more preferably from 28 to 30° C. The initial pH (at 25° C.) of the medium is preferably from 2 to 11, more preferably from 3 to 8.

In the present invention, in order to attain an anaerobic condition, aeration may be performed with one kind of inert gas or a combination of two or more kinds of inert gasses, for example, a nitrogen gas, a helium gas, an argon gas, a hydrogen gas and other inert gasses. Of those, a condition under a nitrogen gas atmosphere or a carbon dioxide gas atmosphere is preferred. The aeration amount may be appropriately set depending on the kind of the inert gas. For example, the aeration amount is preferably from 0.01 to 2 L/min per liter of a culture solution in the case of the nitrogen gas.

The culture period under the anaerobic condition is preferably from 6 to 360 hours, more preferably from 8 to 300 hours.

For example, a buffering agent may be used for the pH adjustment of the medium. Examples of the buffering agent include an organic acid such as acetic acid, citric acid, fumaric acid, malic acid, lactic acid, gluconic acid or tartaric acid, an inorganic acid such as carbonic acid, phosphoric acid, hydrochloric acid, or sulfuric acid, an alkali hydroxide such as sodium hydroxide, ammonia, ammonia water and the like. The buffering agent may be used singly or in combination of two or more kinds thereof, and the amount thereof may be appropriately selected so as to achieve a desired pH.

The *Euglena* may be cultured in the dark or under light irradiation. The light irradiation may be performed under any conditions that enable photosynthesis, and any of artificial light and solar light may be used. The intensity of the light irradiation is preferably from 1,000 to 20,000 Lux, more preferably from 2,000 to 8,000 Lux.

Further, the agitation speed and shaking speed may be appropriately set in consideration of damage to cells, and are typically from 10 to 300 r/min.

<Enzymatic Reaction>

The enzymatic reaction of the protease with the *Euglena* is performed in an aqueous phase. For example, the reaction can be performed by mixing the *Euglena*, protease and water. In addition, the reaction can be performed by adding the protease to a culture solution containing the *Euglena*.

The protease used in the present invention is not particularly limited as long as the protease has a protease activity. Examples thereof may include pepsin, pancreatin, papain, subtilisin, chymotrypsin and the like. In addition, as the protease, a commercially available product may be used. Examples thereof may include PANCIDASE MP and AROASE AP-10 (each manufactured by Yakult Pharmaceutical Industry Co., Ltd.), Protease A "Amano" SD and Protease M "Amano" SD (each manufactured by Amano Enzyme Inc.), Savinase 16.0 EX and Everlase 16L EX (each manufactured by Novozymes), Purafect 4000L (manufactured by Genencor) and the like. It should be noted that one kind of the protease may be used alone, or two or more kinds thereof may be used in combination. In addition, actions may be repeated a plurality of times by using the same kind or different kinds of enzymes.

The protease includes an alkaline protease having an optimum pH in an alkaline region and an acid protease having an optimum pH in an acidic region, but the alkaline protease is preferred because even a small amount of the alkaline protease added can improve the yield of the fatty acid ester.

The alkaline protease is not particularly limited, and examples thereof include alkaline proteases produced by *Bacillus* bacteria (such as *Bacillus halodurans, Bacillus clausii, Bacillus alcalophilus, Bacillus circulans, Bacillus firmus* and *Bacillus halmapalus*).

The amount of the protease added is an amount corresponding to an enzymatic activity within a range of from 0.001 to 9.5 [PU/g-dry cell]. In the present invention, the amount of the protease added is adjusted so as to correspond to an enzymatic activity of 0.001 [PU/g-dry cell] or more, preferably 0.01 [PU/g-dry cell] or more, from the viewpoint of extraction of the fatty acid ester from the cells. In addition, from the viewpoint of improving the yield of the fatty acid ester, the amount of the protease added is adjusted so as to correspond to an enzymatic activity of 9.5 [PU/g-dry cell] or less, preferably 9 [PU/g-dry cell] or less, more preferably 5 [PU/g-dry cell] or less, more preferably 2 [PU/g-dry cell] or less, even more preferably 1 [PU/g-dry cell] or less.

The amount of the protease added is an amount corresponding to an enzymatic activity within a range of from 0.001 to 9.5 [PU/g-dry cell], preferably from 0.001 to 9 [PU/g-dry cell], more preferably from 0.01 to 5 [PU/g-dry cell], more preferably from 0.01 to 2 [PU/g-dry cell], even more preferably from 0.01 to 1 [PU/g-dry cell], from the viewpoints of extraction of the fatty acid aster from the cells and improving the yield of the fatty acid ester. In this description, "1 PU of enzymatic activity" refers to the amount of an enzyme required to release an acid-soluble protein-degraded product corresponding to 1 mmol of tyrosine for 1 minute when the enzyme is allowed to act using casein as a substrate. The "1 PU of enzymatic activity" can be measured using a commercially available kit as described in Examples.

Further, the amount of the protease added with respect to the dry cells of the *Euglena* is preferably from 0.0001 to 4.8 [g-enzyme preparation/g-dry cell], more preferably from 0.0005 to 3 [g-enzyme preparation/g-dry cell], even more preferably from 0.001 to 1 [g-enzyme preparation/g-dry cell], from the viewpoint of improving the yield of the fatty acid ester.

The condition of the enzymatic reaction may be appropriately set in consideration of the optimum condition of the protease used, and for example, the reaction liquid has an initial pH (at 25° C.) of usually from 2 to 12, preferably from 4 to 11, more preferably from 6.5 to 10.5. In addition, the reaction is performed at a temperature of usually from 20 to 80° C., preferably from 30 to 70° C., more preferably from 40 to 60° C., and the reaction is performed for a time of usually from 0.1 to 16 hours, preferably from 0.25 to 8 hours, more preferably from 0.5 to 4 hours.

Step (b)

The step (b) is a step of performing phase separation and collection of a fatty acid ester from a reaction liquid after the step (a).

A method of collecting the fatty acid ester is not particularly limited as long as the fatty acid ester can be fractionated from the reaction liquid, and examples thereof include solvent extraction, centrifugation, static treatment, column chromatography and the like. One of the methods may be employed alone, or two or more kinds thereof may be employed in combination. Of those, from the viewpoint of improving the yield of the fatty acid ester, one kind or a combination of two or more kinds selected from solvent extraction, centrifugation and static treatment is preferred, and a combination of solvent extraction and centrifugation, a combination of solvent extraction and static treatment, or centrifugation is more preferred.

In the solvent extraction, the fatty acid ester can be collected from a reaction liquid by adding an organic solvent to the reaction liquid and performing phase separation of the organic phase and the aqueous phase to collect the organic phase. Examples of the organic solvent used in the solvent extraction include: esters such as methyl acetate and ethyl acetate; linear and cyclic ethers such as tetrahydrofuran and diethyl ether; polyethers such as polyethylene glycol; halogenated hydrocarbons such as dichloromethane, chloroform and carbon tetrachloride; hydrocarbons such as hexane, cyclohexane and petroleum ether; aromatic hydrocarbons such as benzene and toluene; pyridines; supercritical carbon dioxide; alcohols such as butanol, pentanol and hexanol; polyhydric alcohols such as butylene glycol; ketones such as methyl ethyl ketone; and the like. One of the organic solvents may be used alone, or two or more kinds thereof may be used in combination. Further, the solvent extraction may be repeated a plurality of times by using the same kind of or different kinds of solvents.

Of those, a non-polar solvent is preferred from the viewpoints of the solubility of the fatty acid ester and improving the yield. Specific examples thereof include halogenated hydrocarbons, hydrocarbons and aromatic hydrocarbons. Of those, hydrocarbons are preferred, and hexane is more preferred.

Further, an organic solvent compatible with water, such as methanol, ethanol, propanol, ethylene glycol, propylene glycol or acetone, may be used adjunctively.

When the amount of the organic solvent used is too small, it is difficult to perform phase separation of the organic phase and the aqueous phase. Therefore, in general, the solvent extraction is performed with a large amount of the organic solvent. On the other hand, in the present invention, the phase separation of the organic phase and the aqueous phase can be promoted by reducing the amount of the protease used. Therefore, for example, the volume ratio of the organic phase containing the fatty acid ester to the aqueous phase containing the culture solution (organic phase/aqueous phase), which serves as the amount of the organic solvent used, can be reduced to 1 or less. In terms of volume ratio of the organic phase/aqueous phase, the amount of the organic solvent used is preferably from 0.65 to 1, more preferably from 0.75 to 1, even more preferably from 0.85 to 1.

Any of immersion, decoction, leaching, reflux extraction, supercritical extraction, subcritical extraction and the like may be used as an extraction method. It is possible to refer to, for example, the methods described in "Experimental Method for Plant Lipid Metabolism, Biochemical Experimental Method 24" (written and edited by Akihiro Yamada, Japan Scientific Societies Press, p. 3-4).

The temperature of the extraction is not particularly limited, but is preferably from 10 to 50° C., more preferably from 20 to 40° C., from the viewpoint of the extraction efficiency of the fatty acid ester.

The centrifugation can be performed using a general instrument such as a separating plate-type, cylinder-type or decanter-type centrifuge. In this case, the centrifugal force is preferably from 500 to 20,000 G, more preferably from 1,000 to 10,000 G. The centrifugation is performed under a temperature condition of preferably from 10 to 50° C., more preferably from 20 to 40° C. Further, the speed and time of rotation may be appropriately set. For example, in the case of the separating plate-type centrifuge, the rotation speed is preferably from 5,000 to 20,000 r/min, more preferably from 8,000 to 18,000 r/min, and the time of the treatment is preferably from 1 to 30 minutes, more preferably from 1 to 15 minutes.

The static treatment may be performed by maintaining a reaction liquid in a static state until phase separation of the fatty acid ester and the aqueous phase occurs. In the present invention, the fatty acid ester can be fractionated more efficiently by performing the solvent extraction and the static treatment in combination. The temperature for the static treatment is not particularly limited, but is preferably from 10 to 50° C., more preferably from 20 to 40° C. The time for the static treatment may be appropriately set, and is preferably from 30 to 300 minutes, more preferably from 60 to 150 minutes.

In the present invention, the fatty acid ester can be collected through such simple operation from the *Euglena* including the fatty acid ester accumulated in the cells in as high a yield as 75% or more, preferably 80% or more.

When an appropriate amount of the protease is allowed to act on the *Euglena* including the fatty acid ester accumulated, oil-water separation easily occurs, although a detail mechanism thereof is unknown. This is considered to be one of the causes of such effect.

Further, in the present invention, an aliphatic alcohol can be produced by hydrogenating the fatty acid ester collected in the step (b) in the presence of a hydrogenation catalyst.

Any known hydrogenation catalyst may be used as the hydrogenation catalyst used in the present invention. An example thereof is a catalyst containing at least one kind of metal selected from copper, cobalt, chromium, platinum, rhodium, palladium, iridium and the like. Of those, a copper-based catalyst is preferred, and there may be suitably used a copper-chromium-based catalyst, a copper-zinc-based catalyst, a copper-iron-aluminum-based catalyst, a copper-silica-based catalyst or the like.

The hydrogenation catalyst may be used in the form of a solid catalyst in which a catalyst metal is supported on a support such as carbon (activated carbon), alumina, silica-alumina, silica, barium carbonate, barium sulfate, calcium carbonate, titanium oxide, zirconium oxide or zeolite.

A commercially available product may be used as the hydrogenation catalyst, or the hydrogenation catalyst may be prepared by a conventionally known method. For example, the supported solid catalyst may be prepared by a precipitation method, an ion-exchange method, an evaporation-to-dryness method, a spray drying method, a kneading method or the like.

The pressure of hydrogen may be normal pressure, but hydrogenation is preferably performed under increased pressure and is thus performed under a gauge pressure of preferably from 0.1 to 35 MPa, more preferably from 3 to 30 MPa.

The temperature of the reaction is preferably from 30 to 300° C., more preferably from 130 to 270° C., even more preferably from 150 to 250° C. In addition, the time of the reaction is preferably from 0.5 to 7 hours, more preferably from 1 to 6 hours, even more preferably from 3 to 5 hours.

The amount of the hydrogenation catalyst used may be arbitrarily selected depending on the temperature of the reaction or the pressure of the reaction as long as a practical yield of the reaction is obtained. The amount is preferably from 0.1 to 30 parts by mass, more preferably from 0.5 to 20 parts by mass with respect to 100 parts by mass of the fatty acid ester.

The present invention further discloses the following production method regarding the above-mentioned embodiment.

<1>
A method of producing a fatty acid ester, comprising the following steps (a) and (b):
(a) adding 0.001 to 9.5 [PU/g-dry cell] of at least one kind of protease to *Euglena* to react the *Euglena* and the protease in an aqueous phase; and
(b) performing phase separation and collection of a fatty acid ester from a reaction liquid of the step (a).

<2>
The method of producing a fatty acid ester according to Item <1>, in which the protease is preferably alkaline protease.

<3>
The method of producing a fatty acid ester according to Item <1> or <2>, in which, in the step (b), the collection of the fatty acid ester is performed preferably by one kind or a combination of two or more kinds selected from solvent extraction, centrifugation and static treatment, more preferably by solvent extraction and centrifugation, solvent extraction and static treatment, or centrifugation.

<4>
The method of producing a fatty acid ester according to any one of Items <1> to <3>, in which the *Euglena* is preferably *Euglena gracilis*, *Euglena gracilis* var. *bacillaris*, *Euglena viridis*, *Astasia longa*, or a variant species or mutant strain thereof.

<5>
The method of producing a fatty acid ester according any one of Items <1> to <4>, in which, in the step (a), the amount of the protease added is an amount corresponding to an enzymatic activity of preferably 0.001 [PU/g-dry cell] or more, more preferably 0.01 [PU/g-dry cell] or more and of preferably 9.5 [PU/g-dry cell] or less, more preferably 9 [PU/g-dry cell] or less, more preferably 5 [PU/g-dry cell] or less, more preferably 2 [PU/g-dry cell] or less, even more preferably 1 [PU/g-dry cell] or less.

<6>
The method of producing a fatty acid ester according any one of Items <1> to <4>, in which, in the step (a), the amount of the protease added is an amount corresponding to an enzymatic activity within a range of preferably from 0.001 to 9.5 [PU/g-dry cell], more preferably from 0.001 to 9 [PU/g-dry cell], more preferably from 0.001 to 5 [PU/g-dry cell], more preferably from 0.01 to 2 [PU/g-drycell], even more preferably from 0.01 to 1 [PU/g-drycell].

<7>
The method of producing a fatty acid ester according to any one of Items <1> to <4>, in which, in the step (a), the amount of the protease added with respect to the dry cell of the *Euglena* is preferably from 0.0001 to 4.8 [g-enzyme preparation/g-dry cell], more preferably from 0.0005 to 3 [g-enzyme preparation/g-dry cell], even more preferably from 0.001 to 1 [g-enzyme preparation/g-dry cell].

<8>
The method of producing a fatty acid ester according to any one of Items <1> to <7>, in which, in the step (a), the reaction liquid has an initial pH at 25° C. of preferably from 2 to 12, more preferably from 4 to 11, even more preferably from 6.5 to 10.5.

<9>
The method of producing a fatty acid ester according to any one of Items <1> to <8>, in which, in the step (a), the reaction is performed at a temperature of preferably from 20 to 80° C., more preferably 30 to 70° C., even more preferably from 40 to 60° C.

<10>
The method of producing a fatty acid ester according to any one of Items <1> to <9>, in which, in the step (a), the reaction is performed for a time of preferably from 0.1 to 16 hours, more preferably from 0.25 to 8 hours, even more preferably from 0.5 to 4 hours.

<11>
The method of producing a fatty acid ester according any one of Items <3> to <10>, in which, in the step (b), an organic solvent used in the solvent extraction is preferably a non-polar solvent, more preferably a halogenated hydrocarbon, a hydrocarbon or an aromatic hydrocarbon, more preferably a hydrocarbon, even more preferably hexane.

<12>
The method of producing a fatty acid ester according any one of Items <3> to <11>, in which, in the step (b), the amount of the organic solvent used in the solvent extraction is preferably from 0.65 to 1, more preferably from 0.75 to 1, even more preferably from 0.85 to 1 in terms of the volume ratio of organic phase/aqueous phase.

<13>

The method of producing a fatty acid ester according to any one of Items <1> to <12>, in which the *Euglena* used in the step (a) has a content of the fatty acid ester, which is accumulated in the cell of the *Euglena*, of preferably 20 mass % or more, more preferably 40 mass % or more, even more preferably 50 mass % or more based on the dry cell of the *Euglena*.

<14>

The method of producing a fatty acid ester according to any one of Items <1> to <13>, in which the *Euglena* used in the step (a) has a content of the fatty acid ester, which is accumulated in the cell of the *Euglena*, of preferably 90 mass % or less, more preferably 85 mass % or less, even more preferably 80 mass % or less based on the dry cell of the *Euglena*.

<15>

The method of producing a fatty acid ester according to any one of Items <1> to <12>, in which the *Euglena* used in the step (a) has a content of the fatty acid ester, which is accumulated in the cell of the *Euglena*, of preferably from 20 to 90 mass %, more preferably from 40 to 85 mass %, even more preferably from 50 to 80 mass % based on the dry cell of the *Euglena*.

<16>

The method of producing a fatty acid ester according to any one of Items <1> to <15>, further comprising, before the step (a), a step of accumulating a fatty acid ester in the cell of the *Euglena* by culture.

<17>

The method of producing a fatty acid ester according to Item <16>, in which the *Euglena* is inoculated in a medium in an amount of preferably from 0.01 to 10 [g-dry cell/L], more preferably from 0.1 to 5 [g-dry cell/L] with respect to a volume of the medium.

<18>

The method of producing a fatty acid ester according to Item <16> or <17>, in which the culture is performed under an aerobic condition and subsequently under an anaerobic condition.

<19>

The method of producing a fatty acid ester according to any one of Items <16> to <18>, in which the culture is performed at a temperature of preferably from 20 to 33° C., more preferably from 28 to 30° C.

<20>

The method of producing a fatty acid ester according to Item <18> or <19>, in which the medium under the aerobic condition has an initial pH (at 25° C.) of preferably from 2 to 7, more preferably 3 to 5.

<21>

The method of producing a fatty acid ester according to any one of Items <18> to <20>, in which aeration condition for the aerobic condition is preferably from 0.01 to 2 L/min, more preferably from 0.1 to 0.5 L/min per liter of a culture solution.

<22>

The method of producing a fatty acid ester according to any one of Items <18> to <21>, in which the culture under the aerobic condition is performed for a period of preferably from 48 to 720 hours, more preferably from 72 to 360 hours.

<23>

The method of producing a fatty acid ester according to any one of Items <18> to <22>, in which the medium under the anaerobic condition has an initial pH (at 25° C.) of preferably from 2 to 11, more preferably from 3 to 8.

<24>

The method of producing a fatty acid ester according any one of Items <18> to <23>, in which the amount of the aeration of a nitrogen gas under the anaerobic condition is preferably from 0.01 to 2 L/min per liter of a culture solution.

<25>

The method of producing a fatty acid ester according any one of Items <18> to <24>, in which the culture under the anaerobic condition is performed for a period of preferably from 6 to 360 hours, more preferably from 8 to 300 hours.

<26>

The method of producing a fatty acid ester according to any one of Items <1> to <25>, in which the fatty acid ester is preferably an ester of a fatty acid having 10 to 30 carbon atoms and a higher alcohol having 10 to 20 carbon atoms.

<27>

The method of producing a fatty acid ester according to any one of Items <1> to <25>, in which the fatty acid ester is preferably an ester of a fatty acid having 10 to 20 carbon atoms and a higher alcohol having 10 to 16 carbon atoms.

<28>

The method of producing a fatty acid ester according to any one of Items <1> to <25>, in which the fatty acid ester is preferably at least one kind selected from dodecyl decanoate, dodecyl dodecanoate, tetradecyl dodecanoate, dodecyl tetradecanoate, tetradecyl tetradecanoate, hexadecyl tetradecanoate, octadecyl tetradecanoate, dodecyl hexadecanoate, tetradecyl hexadecanoate, hexadecyl hexadecanoate and octadecyl hexadecanoate.

<29>

A method of producing an aliphatic alcohol, comprising hydrogenating the fatty acid ester obtained by the method according to any one of Items <1> to <28> in the presence of a hydrogenation catalyst.

EXAMPLES

Analysis Method

1. Measurement of Protease Activity (Casein Method)

1% Casein (w/v, casein manufactured by Calbiochem, bovine milk, carbohydrate and fatty acid free) was used as a substrate, and 50 mM buffer containing the casein and having an optimum pH was kept at an optimum temperature for 5 minutes. After that, 0.1 mL of an enzyme solution was added thereto and subjected to a reaction for 15 minutes while the temperature was maintained. In this case, the enzyme was diluted with the buffer described above to an appropriate concentration before use. 2.0 mL of a reaction stop solution was added to the reaction liquid, and the mixture was left to stand still for 30 minutes at an optimum temperature and subsequently filtered. 0.5 mL of reagent A' and 4 mL of reagent B, supplied as reagents of DC protein assay (manufactured by Bio-Rad Laboratories, Inc., Lowry method), was added to 0.1 mL of the filtrate, and the mixture was left to stand still at 25° C. for 15 minutes, followed by measurement of an absorbance at 750 nm.

In this case, the term "optimum pH" refers to a pH at which the enzymatic activity is highest, and the term "optimum temperature" refers to a temperature at which the enzymatic activity is highest. It should be noted that, in the case of acid protease, the optimum pH and the optimum temperature are usually from pH 2 to 7.3 and from 20 to 80° C., respectively, and in the case of alkaline protease, the optimum pH and the optimum temperature are usually from pH 8 to 12 and from 20 to 80° C., respectively.

<Measurement of Protease Activity of Alkaline Protease>

1.0 mL of 50 mM borate buffer (pH 10) containing 1% casein (w/v, casein manufactured by Calbiochem, bovine milk, carbohydrate and fatty acid free) was kept at 30° C. for 5 minutes, and 0.1 mL of an enzyme solution was added thereto and subjected to a reaction for 15 minutes while the temperature was maintained. In this case, the enzyme was diluted with 50 mM borate buffer (pH 10) to an appropriate concentration before use. 2.0 mL of a reaction stop solution (0.11 M trichloroacetic acid-0.22 M sodium acetate-0.33 M acetic acid) was added thereto, and the mixture was left to stand still at 30° C. for 30 minutes and filtered using No. 2 filter paper (manufactured by Advantec), followed by determination of the amount of acid-soluble protein-degraded products in the filtrate by DC protein assay (manufactured by Bio-Rad Laboratories, Inc., Lowry method). That is, 0.5 mL of reagent A' and 4 mL of reagent B, supplied as reagents of DC protein assay, were added to the filtrate, and the mixture was left to stand still at 25° C. for 15 minutes, followed by measurement of an absorbance at 750 nm.

<Measurement of Protease Activity of PANCIDASE MP>

An analysis was performed in the same manner as that in the case of the alkaline protease or the like described above, except that 50 mM phosphate buffer (pH 7.2) was used instead of the 50 mM borate buffer (pH 10).

<Creation of Calibration Curve>

L-Tyrosine was dissolved in a buffer so as to achieve a concentration of from 0 to 0.3 mM to prepare L-tyrosine solutions. 0.5 mL of reagent A' and 4 mL of reagent B, supplied as reagents of DC protein assay (manufactured by Bio-Rad Laboratories, Inc., Lowry method), were added to 0.1 mL of each concentration of the L-tyrosine solutions, and the mixtures were left to stand still at 25° C. for 15 minutes, followed by measurement of absorbances at 750 nm to create a calibration curve.

2. Analysis of Fatty Acid Ester

A sample was analyzed by gas chromatography (GC). Conditions are as described below.

Device: Agilent technology 6890N
Column: Ultra-Alloy-1 manufactured by Frontier Laboratories Ltd., MS/HT, 15 m×0.25 mm×0.15 µm
Oven temperature: 60° C. (kept for 2 min)–[temperature rising at 10° C./min]–350° C. (kept for 15 min)
Carrier gas: He (5.8 mL/min)
Injection volume: 1 µL
Split ratio: 14:1
Inlet temperature: 300° C.
Pressure: 185 kPa Then, reagents of dodecyl dodecanoate (manufactured by Wako Pure Chemical Industries, Ltd.), dodecyl hexadecanoate (manufactured by Sigma-Aldrich Corporation), hexadecyl hexadecanoate (manufactured by Sigma-Aldrich Corporation) and hexadecyl tetradecanoate (manufactured by Wako Pure Chemical Industries, Ltd.) were used as standard substances, and the total amount of the fatty acid esters was determined based on area ratios.

3. Analysis of Extraction Rate of Fatty Acid Ester ($E_F$)

800 µL of chloroform was added to 800 µL of the reaction liquid, and the mixture was agitated vigorously at room temperature for 30 minutes and was left to stand still until the chloroform phase was separated from the aqueous phase, or was centrifuged (rotation speed: 15,000 r/min, at a temperature of 25° C. for 3 minutes). Subsequently, the chloroform phase was fractionated, and the mass ($C_F$) of the fatty acid ester in the chloroform phase was analyzed and was defined as an extraction rate of the fatty acid ester of 100%. Next, 800 µL of hexane was added to 800 µL of the reaction liquid, and the mixture was subjected to extraction with hexane in the same manner as that in the extraction with chloroform described above, followed by an analysis of the mass ($H_F$) of the fatty acid ester in the hexane phase. Then, the extraction rate of the fatty acid ester was calculated on the basis of the following equation.

Extraction rate of fatty acid ester(%)=$H_F/C_F\times100$ (In the equation, $H_F$ represents the mass of the fatty acid ester in the hexane phase, and $C_F$ represents the mass of the fatty acid ester in the chloroform phase.)

4. Calculation of Recovery Rate of Solvent ($R_F$)

The recovery rate of the solvent was calculated on the basis of the following equation.

Recovery rate of solvent(%)=$R_H/A_H\times100$ (In the equation, $R_H$ represents the mass of the hexane phase recovered, and $A_H$ represents the mass of hexane added.)

5. Calculation of Yield of Fatty Acid Ester

The yield of the fatty acid ester was calculated on the basis of the following equation.

Yield of fatty acid ester(%)=$(E_F/100)\times(R_F/100)\times100$ (In the equation, $E_F$ represents the extraction rate of the fatty acid ester (%), and $R_F$ represents the recovery rate of the solvent (%).)

6. Calculation of Recovery Rate of Fatty Acid Ester ($S_F$)

1,500 µL of the reaction liquid was centrifuged (rotation speed: 15,000 r/m, at a temperature of 25° C. for 3 minutes), and the upper phase was fractionated. 800 µL of chloroform was added thereto, and the mixture was agitated vigorously at room temperature for 30 minutes and was centrifuged (rotation speed: 15,000 r/min, at a temperature of 25° C. for 3 minutes). Subsequently, the chloroform phase was fractionated, and the mass ($B_F$) of the fatty acid ester in the chloroform phase was analyzed. Then, the recovery rate of the fatty acid ester was calculated on the basis of the following equation.

Recovery rate of fatty acid ester(%)=$B_F/C_F\times100$ (In the equation, $B_F$ represents the mass of the fatty acid ester in the chloroform phase, which is obtained by extraction of the upper phase fractionated from the reaction liquid, and $C_F$ represents the mass of the fatty acid ester in the chloroform phase, which is obtained by extraction of the reaction liquid.)

7. Calculation of Yield of Fatty Acid Ester

The yield of the fatty acid ester was calculated on the basis of the following equation.

Yield of fatty acid ester(%)=$(E_F/100)\times(S_F/100)\times100$ (In the equation, $E_F$ represents the extraction rate of the fatty acid ester (%), and $S_F$ represents the recovery rate of the fatty acid ester (%).)

Culture of *Euglena*

Production Example 1

5 L of a liquid medium containing 100 g of glucose, 25.0 g of polypeptone, 1.25 g of ammonium sulfate, 1.25 g of potassium dihydrogen phosphate, 2.50 g of magnesium sulfate heptahydrate, 0.600 g of calcium carbonate, 0.250 g of disodium dihydrogen ethylenediaminetetraacetate (EDTA.2Na), 0.250 g of ammonium iron(II) sulfate hexahydrate, 0.125 g of zinc sulfate, 0.090 g of manganese sulfate pentahydrate, 12.5 mg of thiamine hydrochloride and 5 µg of cyanocobalamin was prepared. Subsequently, 1.5 L of the liquid medium prepared was collected and loaded into a jar fermenter having a volume of 2 L, and the pH (at 25° C.) of the medium was adjusted to 4.5 with 1 N hydrochloric acid. After that, the medium was sterilized by heating at 121° C. for 30 minutes.

To the sterilized medium, 40 mL of a culture solution of *Euglena gracilis* that had been cultured in another medium having the same composition as the medium was inoculated (amount of *Euglena*: 0.15 g-dry cell/L), and *Euglena gracilis* was subjected to aeration-agitation culture at 28° C. in the dark for 4 days. In this case, the culture was performed at an aeration flow rate of 500 mL/min at an agitation rotation speed of 150 r/min.

After that, the culture was further continued for 11 days under the same conditions as described above, except of switching to nitrogen aeration at 500 mL/min. The content of *Euglena* in the resultant culture solution was 5.4 [g-dry cell/L], and the content of the fatty acid ester accumulated in the cells of the *Euglena* was 74 mass % based on the dry cells. The initial pH (at 25° C.) of the culture solution on switching to nitrogen aeration was 3.4. It should be noted that NIES-48 supplied from the Microbial Culture Collection at the National Institute for Environmental Studies was used as *Euglena gracilis*.

The resultant culture solution was used in Examples and Comparative Examples 1, 3 and 4.

Production Example 2

The same procedure as in Production Example 1 was performed to produce a culture solution. The content of *Euglena* in the culture solution was 5.1 [g-dry cell/L], and the content of the fatty acid ester accumulated in the cells of the *Euglena* was 76 mass % based on the dry cells.

The resultant culture solution was used in Comparative Example 2.

Example 1

1.00 mg (0.020 mass % in terms of the concentration of the enzyme in the culture solution) of an enzyme (manufactured by Yakult Pharmaceutical Industry Co., Ltd.: PANCIDASE MP) was added to 5.00 g of the culture solution, and the mixture was agitated well. The initial pH (at 25° C.) of the solution was 7.3.

Next, 800 μL of the culture solution containing the enzyme added was dispensed in an Eppendorf tube and was left to stand still at 40° C. for 120 minutes to perform an enzymatic reaction.

The reaction liquid was cooled to 25° C. and was subjected to extraction with hexane, yielding a fatty acid ester as a hexane phase.

The resultant fatty acid ester was analyzed on "3. Extraction rate of fatty acid ester," "4. Recovery rate of solvent," and "5. Yield of fatty acid ester" described above. It should be noted that the mass of the hexane phase recovered and the mass of the fatty acid ester in the hexane phase were measured using the hexane phase in an amount corresponding to four Eppendorf tubes, and average values per Eppendorf tube were determined. Further, in the analysis of "3. Extraction rate of fatty acid ester," the operation for phase separation was performed by still standing. Table 1 shows the results of the analysis.

Example 2

A fatty acid ester was obtained as a hexane phase in the same manner as that in Example 1, except that the amount of the enzyme (PANCIDASE MP) added was changed to 5.00 mg (0.10 mass % in terms of the concentration of the enzyme in the culture solution). Table 1 shows the results of the analysis.

Example 3

A fatty acid ester was obtained as a hexane phase in the same manner as that in Example 1, except that the amount of the enzyme (PANCIDASE MP) added was changed to 0.125 g (2.5 mass % in terms of the concentration of the enzyme in the culture solution). Table 1 shows the results of the analysis.

Example 4

A fatty acid ester was obtained as a hexane phase in the same manner as that in Example 1, except that 150 μL (0.0030 mass % in terms of the concentration of an enzyme in the culture solution) of an aqueous solution containing 0.100 mass % of an enzyme (manufactured by Kao Corporation: alkaline protease) was added instead of PANCIDASE to 5.00 g of the culture solution having an initial pH at a liquid temperature of 25° C. adjusted to 10 with sodium hydroxide, the mixture was agitated well, and the temperature of the enzymatic reaction was set to 50° C. Table 1 shows the results of the analysis.

Example 5

A fatty acid ester was obtained as a hexane phase in the same manner as that in Example 1, except that 250 μL (0.0095 mass % in terms of the concentration of an enzyme in the culture solution) of an aqueous solution containing 0.189 mass % of an enzyme (manufactured by Novozymes: Everlase 16L EX) was added instead of PANCIDASE to 5.00 g of the culture solution having an initial pH at a liquid temperature of 25° C. adjusted to 10 with sodium hydroxide, the mixture was agitated well, the temperature of the enzymatic reaction was set to 50° C., and the operation for phase separation in the analysis of "3. Extraction rate of fatty acid ester" was performed by centrifugation. Table 1 shows the results of the analysis.

Example 6

A fatty acid ester was obtained as a hexane phase in the same manner as that in Example 1, except that 250 μL (0.0048 mass % in terms of the concentration of an enzyme in the culture solution) of an aqueous solution of 0.0960 mass % of an enzyme (manufactured by Genencor: Purafect 4000L) was added instead of PANCIDASE to 5.00 g of the culture solution having an initial pH at a liquid temperature of 25° C. adjusted to 10 with sodium hydroxide, the mixture was agitated well, the temperature of the enzymatic reaction was set to 50° C., and the operation for phase separation in the analysis of "3. Extraction rate of fatty acid ester" was performed by centrifugation. Table 1 shows the results of the analysis.

Comparative Example 1

The culture solution was cooled to 25° C. without performing the enzyme treatment and was subsequently subjected to extraction with hexane, yielding a fatty acid ester as a hexane phase.

The analysis of "3. Extraction rate of fatty acid ester" described above was performed. The mass of the hexane phase recovered and the mass of the fatty acid ester in the hexane phase were measured using the hexane phase in an amount corresponding to four Eppendorf tubes, and average values per Eppendorf tube were determined. Further, the operation for phase separation in the analysis of "3. Extraction rate of fatty acid ester" was performed by centrifugation. Table 1 shows the results of the analysis.

Comparative Example 2

100 g of the culture solution was mechanically crushed using a wet type atomization unit (Star Burst manufactured by SUGINO MACHINE LIMITED, type HJP-25001, ball-collision chamber). In this case, the treatment was performed under the following conditions: injection pressure: 50 MPa, chamber nozzle diameter: 0.25 mm, and the number of times of pass: 2. The resultant solution treated was subjected to the same operations as that in Comparative Example 1, yielding a fatty acid ester as a hexane phase. Table 1 shows the results of the analysis.

Comparative Example 3

A fatty acid ester was obtained in the same manner as that in Example 1, except that the amount of the enzyme (PANCIDASE MP) added was changed to 0.250 g (5 mass % in terms of the concentration of the enzyme in the culture solution). Table 1 shows the results of the analysis.

TABLE 1

| | | | | Example 1 | Example 2 | Example 3 | Example 4 | Example 5 |
|---|---|---|---|---|---|---|---|---|
| Material | Microalga | Species | | *Euglena* | *Euglena* | *Euglena* | *Euglena* | *Euglena* |
| | | Concentration | (g-dry cell/L) | 5.4 | 5.4 | 5.4 | 5.4 | 5.4 |
| | Mechanical crushing | Device | | — | — | — | — | — |
| | | Pressure | (MPa) | — | — | — | — | — |
| | | Nozzle diameter | (mm) | — | — | — | — | — |
| | | Pass | (times) | — | — | — | — | — |
| Step (a) | Enzymatic crushing | Enzyme | | PANCIDASE[1] | PANCIDASE[1] | PANCIDASE[1] | Alkaline protease[2] | Everlase[3] |
| | | Concentration of enzyme added | (mass %) | 0.020 | 0.10 | 2.5 | 0.0030 | 0.0095 |
| | | Activity of enzyme | (PU/g-dry cell) | 0.075 | 0.37 | 9.3 | 0.024 | 0.091 |
| | | Temperature | (° C.) | 40° C. | 40° C. | 40° C. | 50° C. | 50° C. |
| | | Initial pH | | 7.3 | 7.3 | 7.3 | 10 | 10 |
| | | Time | (min) | 120 | 120 | 120 | 120 | 120 |
| Step (b) | Solvent extraction | Solvent | | Hexane | Hexane | Hexane | Hexane | Hexane |
| | | Organic phase/aqueous phase | (volume ratio) | 1.0 | 1.0 | 1.0 | 1.0 | 1.0 |
| | | Temperature | (° C.) | 25 | 25 | 25 | 25 | 25 |
| | | Time | (min) | 30 | 30 | 30 | 30 | 30 |
| | Still standing | Temperature | (° C.) | 25 | 25 | 25 | — | — |
| | | Time for still standing | (min) | 120 | 120 | 120 | — | — |
| | Centrifugation | Rotation speed | (r/min) | — | — | — | 15,000 | 15,000 |
| | | Temperature | (° C.) | — | — | — | 25 | 25 |
| | | Time | (min) | — | — | — | 3 | 3 |
| | Results | Extraction rate of fatty acid ester | (%) | 89 | 96 | 98 | 86 | 93 |
| | | Yield of fatty acid ester | (%) | 82 | 86 | 79 | 83 | 88 |
| | | Recovery rate of solvent | (%) | 92 | 90 | 81 | 96 | 95 |

| | | | | Example 6 | Comparative Example 1 | Comparative Example 2 | Comparative Example 3 |
|---|---|---|---|---|---|---|---|
| Material | Microalga | Species | | *Euglena* | *Euglena* | *Euglena* | *Euglena* |
| | | Concentration | (g-dry cell/L) | 5.4 | 5.4 | 5.2 | 5.4 |
| | Mechanical crushing | Device | | — | — | Star Burst | — |
| | | Pressure | (MPa) | — | — | 50 | — |
| | | Nozzle diameter | (mm) | — | — | 0.25 | — |
| | | Pass | (times) | — | — | 2 | — |
| Step (a) | Enzymatic crushing | Enzyme | | Purafect[4] | — | — | PANCIDASE[1] |
| | | Concentration of enzyme added | (mass %) | 0.0048 | — | — | 5.0 |
| | | Activity of enzyme | (PU/g-dry cell) | 0.029 | — | — | 18.5 |
| | | Temperature | (° C.) | 50° C. | — | — | 40° C. |
| | | Initial pH | | 10 | — | — | 7.3 |
| | | Time | (min) | 120 | — | — | 120 |
| Step (b) | Solvent extraction | Solvent | | Hexane | Hexane | Hexane | Hexane |
| | | Organic phase/aqueous phase | (volume ratio) | 1.0 | 1.0 | 1.0 | 1.0 |
| | | Temperature | (° C.) | 25 | 25 | 25 | 25 |
| | | Time | (min) | 30 | 30 | 30 | 30 |
| | Still standing | Temperature | (° C.) | — | — | — | 25 |
| | | Time for still standing | (min) | — | — | — | 120 |

TABLE 1-continued

|  |  |  |  |  |  |  |
|---|---|---|---|---|---|---|
| Centrifugation | Rotation speed | (r/min) | 15,000 | 15,000 | 15,000 | — |
|  | Temperature | (° C.) | 25 | 25 | 25 | — |
|  | Time | (min) | 3 | 3 | 3 | — |
| Results | Extraction rate of fatty acid ester | (%) | 98 | 5.0 | 91 | 97 |
|  | Yield of fatty acid ester | (%) | 92 | 3.7 | 72 | 2.9 |
|  | Recovery rate of solvent | (%) | 94 | 74 | 79 | 3.0 |

[1] Produce name: PANCIDASE MP, manufactured by Yakult Pharmaceutical Industry Co., Ltd.
[2] Produce name: Alkaline protease, manufactured by Kao Corporation
[3] Produce name: Everlase 16L EX, manufactured by Novozymes
[4] Produce name: Purafect 4000L, manufactured by Genencor

Example 7

625 µL (0.0050 mass % in terms of the concentration of an enzyme added in the culture solution) of an aqueous solution containing 0.100 mass % of an enzyme (manufactured by Kao Corporation: alkaline protease) was added to 12.5 g of a culture solution having an initial pH at a liquid temperature of 25° C. adjusted to 10 with sodium hydroxide, and the mixture was agitated well. The reaction liquid was left to stand still at an enzymatic reaction temperature of 60° C. for 60 minutes to perform an enzymatic reaction. The reaction liquid was cooled to 25° C. and centrifuged, yielding a fatty acid ester as an upper phase liquid.

The resultant was analyzed on the "3. Fatty acid ester extraction rate" described above. In this case, the operation for phase separation was performed by centrifugation. Further, the reaction liquid cooled was analyzed on the "6. Recovery rate of fatty acid ester" and "7. Yield of fatty acid ester." Table 2 shows the results of the analysis.

Comparative Example 4

The culture solution was left to stand still at a temperature of 60° C. for 60 minutes without performing the enzyme treatment. Subsequently, the culture solution was cooled to 25° C. and centrifuged, yielding a fatty acid ester as an upper phase liquid.

The resultant culture solution was analyzed by the same operation as that in Example 7. Table 2 shows the results of the analysis.

TABLE 2

|  |  |  |  | Example 7 | Comparative Example 4 |
|---|---|---|---|---|---|
| Material | Microalga | Species |  | *Euglena* | *Euglena* |
|  |  | Concentration | (g-dry cell/L) | 5.4 | 5.4 |
|  | Mechanical crushing |  |  | — | — |
| Step (a) | Enzymatic crushing | Enzyme |  | Alkaline protease[2] | — |
|  |  | Amount of enzyme added | (mass %) | 0.0050 | — |
|  |  | Activity of enzyme | (PU/g-dry cell) | 0.041 | — |
|  |  | Temperature | (° C.) | 60° C. | — |
|  |  | Initial pH |  | 10 | — |
|  |  | Time | (min) | 60 | — |
| Step (b) | Solvent extraction |  |  | — | — |
|  | Still standing |  |  | — | — |
|  | Centrifugation | Rotation speed | (r/min) | 15,000 | 15,000 |
|  |  | Temperature | (° C.) | 25 | 25 |
|  |  | Time | (min) | 3 | 3 |
|  | Results | Extraction rate of fatty acid ester | (%) | 85 | 7.4 |
|  |  | Yield of fatty acid ester | (%) | 78 | 5.7 |
|  |  | Recovery rate of fatty acid ester | (%) | 92 | 77 |

[2] Produce name: Alkaline protease, manufactured by Kao Corporation

As apparent from Table 1 and Table 2, the fatty acid ester was able to be collected from the *Euglena* in a high yield according to the method of the present invention. On the other hand, in Comparative Example 1 and Comparative Example 4 in which the *Euglena* was not subjected to any of the mechanical crushing and the enzymatic crushing, the fatty acid ester was not taken out of the cells, and the yields were low. In addition, in Comparative Example 2 in which the *Euglena* was subjected to only the mechanical crushing and in Comparative Example 3 in which the *Euglena* was subjected to a reaction with a high concentration of the protease, it was difficult to fractionate the fatty acid ester taken out of the cells, and the yields were low.

The invention claimed is:
1. A method of obtaining fatty acid esters from *Euglena*, comprising the following steps (a)-(d):
   (a) adding 0.001 to 9.5 [PU/g-dry cell] of at least one kind of protease to *Euglena;*
   (b) reacting the *Euglena* with the at least one protease in an aqueous phase to form a reaction liquid;

(c) obtaining a fatty acid ester containing phase by performing phase separation on the reaction liquid; and (d) collecting the fatty acid ester containing phase.

2. The method of claim 1, wherein the protease is an alkaline protease.

3. The method of claim 1, wherein the fatty acid ester containing phase is obtained by solvent extraction.

4. The method of claim 1, wherein the fatty acid ester containing phase is obtained by centrifugation.

5. The method of claim 1, wherein the *Euglena* is *Euglena gracilis*, *Euglena gracilis* var. *bacillaris*, *Euglena viridis* or *Astasia longa*.

6. The method of claim 1, wherein the amount of the protease added with respect to the dry cell of the *Euglena* is from 0.0001 to 4.8 [g-enzyme preparation/g-dry cell].

7. The method of claim 1, wherein the amount of the protease added with respect to the dry cell of the *Euglena* is from 0.0005 to 3 [g-enzyme preparation/g-dry cell].

8. The method of claim 1, wherein the reaction liquid has an initial pH of from 2 to 12 at 25° C.

9. The method of claim 1, wherein the reaction is performed at a temperature of from 20 to 80° C.

10. The method of claim 1, wherein the reaction is performed for from 0.1 to 16 hours.

11. The method of claim 1, wherein the *Euglena* used has a content of fatty acid ester from 20 to 90 mass % based on dry cell weight.

12. The method of claim 1, wherein the *Euglena* is present in a medium in an amount from 0.01 to 10 [g-dry cell/L] with respect to a volume of the medium.

13. The method of claim 1, further comprising culturing *Euglena* at a temperature of from 20 to 33° C.

14. The method of claim 1, further comprising culturing *Euglena* under aerobic conditions followed by anaerobic conditions.

15. The method of claim 14, wherein the medium used under aerobic conditions has an initial pH at 25° C. of from 2 to 7.

16. The method of claim 14, wherein the aerobic conditions comprise aeration at 0.01 to 2 L of gas/min per liter of a culture solution.

17. The method of claim 14, wherein the aerobic conditions are for a period of 48 to 720 hours.

18. The method of claim 14, wherein the medium used under anaerobic conditions has an initial pH at 25° C. of from 2 to 11.

19. The method of claim 1, wherein the fatty acid esters comprise C10 to C30 fatty acids esterified with C10 to C20 alcohols.

20. A method of producing an aliphatic alcohol, comprising:
(a) adding 0.001 to 9.5 [PU/g-dry cell] of at least one kind of protease to *Euglena*;
(b) reacting the *Euglena* with the at least one protease in an aqueous phase to form a reaction liquid;
(c) obtaining a fatty acid ester containing phase by performing phase separation on the reaction liquid;
(d) collecting the fatty acid ester containing phase; and
(e) hydrogenating the collected fatty acid ester using a hydrogenation catalyst.

* * * * *